US010092779B2

(12) United States Patent
Fontana et al.

(10) Patent No.: US 10,092,779 B2
(45) Date of Patent: Oct. 9, 2018

(54) ORAL CARE COMPOSITION COMPRISING CAPSULES

(75) Inventors: Jose Eder Fontana, Sao Paulo (BR); Edilberto Lemos, Sao Paulo (BR); Henrique Jorge Sousa Sales, Sao Paulo (BR); Marcia Pereira, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 556 days.

(21) Appl. No.: 13/058,726

(22) PCT Filed: Aug. 11, 2009

(86) PCT No.: PCT/US2009/053422
§ 371 (c)(1),
(2), (4) Date: May 19, 2011

(87) PCT Pub. No.: WO2010/019587
PCT Pub. Date: Feb. 18, 2010

(65) Prior Publication Data
US 2012/0121669 A1 May 17, 2012

Related U.S. Application Data

(60) Provisional application No. 61/087,762, filed on Aug. 11, 2008.

(51) Int. Cl.
A61K 8/11 (2006.01)
A61K 8/21 (2006.01)
A61K 8/40 (2006.01)
A61K 8/97 (2017.01)
A61Q 11/00 (2006.01)
A61K 8/34 (2006.01)
A61K 8/73 (2006.01)

(52) U.S. Cl.
CPC .............. *A61Q 11/00* (2013.01); *A61K 8/11* (2013.01); *A61K 8/345* (2013.01); *A61K 8/73* (2013.01); *A61K 8/731* (2013.01)

(58) Field of Classification Search
CPC .......... A61K 8/11; A61K 8/345; A61K 8/731; A61K 8/73; A61Q 11/00
USPC ................. 424/401, 54, 58, 49, 52
See application file for complete search history.

(56) References Cited

U.S. PATENT DOCUMENTS

| | | |
|---|---|---|
| 3,535,421 A | 10/1970 | Briner et al. |
| 3,538,230 A | 11/1970 | Morton |
| 3,678,154 A | 7/1972 | Widder et al. |
| 3,696,191 A | 10/1972 | Weeks |
| 3,862,307 A | 1/1975 | Di Giulio |
| 3,937,807 A | 2/1976 | Haefele |
| 3,959,458 A | 5/1976 | Agricola et al. |
| 3,991,177 A | 11/1976 | Vidra et al. |
| 4,058,595 A | 11/1977 | Colodney |
| 4,154,815 A | 5/1979 | Pader |
| 4,340,583 A | 7/1982 | Wason |
| 4,355,022 A | 10/1982 | Rabussay |
| 4,427,652 A | 1/1984 | Gaffar et al. |
| 4,749,562 A | 6/1988 | Lane et al. |
| 4,765,984 A | 8/1988 | Vellekoop et al. |
| 4,816,245 A | 3/1989 | Gaffar et al. |
| 4,842,847 A | 6/1989 | Amjad |
| 4,866,161 A | 9/1989 | Sikes et al. |
| 4,885,155 A | 12/1989 | Parran, Jr. et al. |
| 4,992,420 A | 2/1991 | Neeser |
| 5,000,939 A | 3/1991 | Dring et al. |
| 5,004,597 A | 4/1991 | Majeti et al. |
| 5,290,542 A | 3/1994 | Liang |
| 5,292,526 A | 3/1994 | Gaffar et al. |
| 5,300,305 A | 4/1994 | Stapler et al. |
| 5,302,373 A | 4/1994 | Giacin et al. |
| 5,435,023 A | 7/1995 | Wagner et al. |
| 5,455,023 A | 10/1995 | Giacin et al. |
| 5,562,939 A | 10/1996 | Lewis |
| 5,700,449 A | 12/1997 | Katayama et al. |
| 5,741,773 A | 4/1998 | Zhang et al. |
| 5,840,338 A | 11/1998 | Roos et al. |
| 5,976,507 A * | 11/1999 | Wong et al. ................ 424/52 |
| 6,106,883 A | 8/2000 | Sokolik et al. |
| 6,214,320 B1 | 4/2001 | Gaffar et al. |
| 6,534,091 B1 * | 3/2003 | Garces Garces ........ A61K 8/11 264/4.3 |
| 6,669,929 B1 | 12/2003 | Boyd et al. |
| 7,041,277 B2 | 5/2006 | Holme et al. |
| 7,390,518 B2 | 6/2008 | Gebreselassie et al. |
| 8,178,481 B2 | 5/2012 | Sans et al. |
| 8,178,483 B2 | 5/2012 | Masters et al. |
| 2002/0187190 A1 | 12/2002 | Cade et al. |
| 2003/0091514 A1 | 5/2003 | Stier et al. |
| 2004/0013723 A1 | 1/2004 | Parkh et al. |
| 2004/0146465 A1* | 7/2004 | Fujisawa ................ 424/49 |
| 2004/0247646 A1 | 12/2004 | Ivory et al. |
| 2005/0019273 A1 | 1/2005 | Boyd et al. |
| 2005/0271602 A1 | 12/2005 | Milanovich et al. |
| 2006/0093559 A1 | 5/2006 | Fabry et al. |
| 2006/0120975 A1 | 6/2006 | Scherl et al. |
| 2006/0127329 A1 | 6/2006 | Xu et al. |
| 2006/0134018 A1 | 6/2006 | Trivedi et al. |
| 2006/0134020 A1 | 6/2006 | Robinson et al. |
| 2006/0134023 A1 | 6/2006 | Pilch et al. |
| 2006/0140880 A1 | 6/2006 | Subramanyam et al. |
| 2006/0140883 A1 | 6/2006 | Trivedi et al. |
| 2006/0193791 A1 | 8/2006 | Boyd et al. |
| 2006/0210489 A1 | 9/2006 | Subramanyam et al. |

(Continued)

FOREIGN PATENT DOCUMENTS

| | | |
|---|---|---|
| CN | 1764436 | 4/2006 |
| CN | 1889916 | 1/2007 |

(Continued)

OTHER PUBLICATIONS

Pader, 1988, 1988, *Oral Hygiene Products and Practice—Cosmetic Science and Technology Series* vol. 6, pp. 489-516.

(Continued)

*Primary Examiner* — Doan T Phan

(57) ABSTRACT

Oral care compositions comprising a capsules comprising flavoring and/or one or more active ingredients, and/or flavours, said capsules distributed in an orally acceptable vehicle or carrier.

21 Claims, No Drawings

(56) References Cited

U.S. PATENT DOCUMENTS

| | | |
|---|---|---|
| 2006/0233722 A1 | 10/2006 | Subramanyam et al. |
| 2006/0286044 A1 | 12/2006 | Robinson et al. |
| 2007/0020201 A1 | 1/2007 | Boyd et al. |
| 2007/0020342 A1 | 1/2007 | Modak et al. |
| 2007/0041914 A1 | 2/2007 | Gaffar et al. |
| 2007/0092454 A1 | 4/2007 | Cameron et al. |
| 2007/0104659 A1 | 5/2007 | Yasuda et al. |
| 2007/0104660 A1 | 5/2007 | Miksa et al. |
| 2007/0148213 A1 | 6/2007 | Ibrahim et al. |
| 2007/0253919 A1 | 11/2007 | Boyd et al. |
| 2007/0292502 A1 | 12/2007 | Chang et al. |
| 2008/0014224 A1 | 1/2008 | Boyd et al. |
| 2008/0242767 A1 | 10/2008 | Masters et al. |
| 2010/0055175 A1 | 3/2010 | Nugent |

FOREIGN PATENT DOCUMENTS

| | | | |
|---|---|---|---|
| EP | 0186148 | 7/1986 | |
| EP | 186148 A2 * | 7/1986 | ............... C11D 9/04 |
| EP | 1064910 | 1/2001 | |
| EP | 1064911 | 1/2001 | |
| EP | 1064912 | 1/2001 | |
| EP | 0711544 | 6/2001 | |
| EP | 992672 | 6/2001 | |
| EP | 1129771 | 9/2001 | |
| EP | 1030734 B1 * | 8/2003 | |
| GB | 1309026 | 3/1973 | |
| GB | 1516525 | 7/1978 | |
| GB | 2224204 | 2/1990 | |
| JP | S49-000453 | 1/1974 | |
| JP | S61-225115 A | 10/1986 | |
| JP | H09-227348 A | 9/1997 | |
| TW | 412425 | 11/2000 | |
| WO | WO 97/48288 | 12/1997 | |
| WO | WO 99/059535 | 11/1999 | |
| WO | WO 9959535 A1 * | 11/1999 | ............... A61K 7/16 |
| WO | WO 04/006896 | 1/2004 | |
| WO | WO 04/087089 | 10/2004 | |
| WO | WO 06/031943 | 3/2006 | |
| WO | WO 2006/125262 | 11/2006 | |
| WO | WO 2006/125661 | 11/2006 | |
| WO | WO 2006136196 A1 * | 12/2006 | |
| WO | WO-2006136197 A1 * | 12/2006 | ............. A24D 3/048 |
| WO | WO 2007012981 A2 * | 2/2007 | ............... A61K 8/11 |
| WO | WO 2007/107573 | 9/2007 | |
| WO | WO 08/016855 | 2/2008 | |

OTHER PUBLICATIONS

Written Opinion in International Application No. PCT/US09/053422, dated Feb. 11, 2011.

Cross et al., "Evaluation of the recurrence of denture stomatitis and Candida colonization in a small group of patients who received itraconazole," Oral Surgery, Oral Medicine, Oral Pathology, Oral Radiology and Endodontology vol. 97, Issue 3 , pp. 351-358, Mar. 2004.

Hanawa et al., "Development of Patient-Friendly Preparations: Preparation of a New Allopurinol Mouthwash Containing Polyethylene(oxide) and Carrageenan," Drug Development and Industrial Pharmacy, 2004, vol. 30, No. 2 , pp. 151-161.

International Search Report for PCT/US2009/053422 dated Feb. 4, 2010.

Sherbrooke et al., 1974, "Jojoba: A Wax-Producing Shrub of the Sonoran Desert," Arid Lands Resource Information Paper No. 5, University of Arizona, Office of Arid Lands Studies, Tucson, Arizona.

Urban et al., 2004, "An injectable calcium sulfate-based bone graft putty using hydroxypropylmethylcellulose as the plasticizer," Orthopedics 27(Suppl. 1):s155-s159, Abstract.

* cited by examiner

ORAL CARE COMPOSITION COMPRISING CAPSULES

CROSS-REFERENCE TO RELATED APPLICATIONS

The present application is a national stage entry under 35 U.S.C. § 317 of International Patent Application No. PCT/US2009/053422, filed Aug. 11, 2009, which claims priority to U.S. Provisional Application No. 61/087,762, filed Aug. 11, 2008, the entireties of which are hereby incorporated by reference.

BACKGROUND OF THE INVENTION

Oral care compositions that may be employed for either/both therapeutic or/and cosmetic purposes, come in many forms. These compositions are offered as liquid solutions for use as mouthwashes, mouth rinses, gargling solutions, sprays or liquid tooth whiteners; as pastes, powders or gels for use as toothpastes or dental or periodontal gels; as dissolvable, partially-dissolvable or non-dissolvable films or strips (e.g., a whitening strip); as wafers; as chewing gums; as dental floss; or in other forms.

In many of these forms, the compositions are expected to supply a flavor that is refreshing to the mouth upon use, as well as to cleanse the oral cavity and provide antibacterial and/or antimicrobial, anti-inflammatory, anti-sensitivity and/or tooth whitening benefits, and/or protection against the accumulation plaque and/or dental caries, reducing levels bacteria in the mouth, remineralizing teeth, inhibiting or reducing gingivitis, masking or treating halitosis, promoting healing of sores or cuts in the mouth, reducing and/or maintaining desirable pH levels in the mouth, and/or reduction and/or elimination of other dental problems. Many of these compositions comprise multiple active and/or supportive components in different physical forms, such as combinations of aqueous and oil phases, liquids and pastes containing embedded particles and/or microcapsules, combinations of different solid forms, and the like.

In addition, aesthetic effects have been acknowledged to play an important role in consumer acceptance of these compositions. In many case, ornamental effects have been used to distinguish particular products in the marketplace, and to identify products having distinct properties. In the dentifrice field, substantially clear dentifrice products, such as toothpastes and gels, which have incorporated therein contrasting colored particles or flakes are known. These particles provide an aesthetic effect that the consumer finds pleasing and that promotes the use of the dentifrice, particularly by children. Although such products have met with consumer approval, the art seeks to further improve, the aesthetic effects, well as the cosmetic and therapeutic benefits of these products so as to encourage the use of dentifrices to promote good oral hygiene.

It has now surprisingly been found that a paste or gel dentifrice has been developed that contains possibly-colored encapsulated menthol and/or one or more active ingredients that will be stable in the container, then dissolve, releasing a burst of mouth-refreshing flavor and possibly other benefits upon brushing or other action by the user upon introduction of it into the oral cavity.

BRIEF SUMMARY OF THE INVENTION

This invention encompasses oral care compositions and methods of using the same that are effective in cleaning the oral cavity, and which provide improved methods of promoting oral health.

The invention comprises Composition 1.0, an oral composition comprising capsules encapsulating one or more orally active ingredients, and/or flavors, distributed in an orally acceptable vehicle or carrier.

Other embodiments of the present invention include the following compositions:

1.1 Composition 1.0 wherein the capsules comprise a matrix and a plasticizer.
1.2 Compositions 1.1, wherein the matrix material is a polymer.
1.3 Compositions 1.1-1.2 wherein the matrix material is a polysaccharide.
1.4 Compositions 1.1-1.3 wherein the matrix material is chitosan, algin, agar, and combinations thereof.
1.5 Compositions 1.0-1.4 wherein the plasticizer is an oil, e.g., mineral oil, naphthenic oil, a plant extract, e.g., shea butter, macadamia ternifolia seed oil, jojoba (*Buxus chinensis*) oil, peanut oil, polymers, including polysaccharides, and humectants, such as glycerin, propylene glycol, polyols, e.g., sorbitol, xylitol, and maltitol, polyethers, and combinations thereof.
1.6 Compositions 1.0-1.5 wherein the capsules further comprise a vitamin.
1.7 Compositions 1.0-1.6 wherein the capsules further comprise excipients and inter ingredients, e.g., such as vitamins (e.g., tocopherol), and excipients and inert ingredients, e.g., binders, tillers, anti-caking agents, disintegrants, colorants, flavorants, odorants, enzymes, coatings (e.g., enteric, acrylic, or carbohydrate or cellulosic coatings), chelants, preservatives (e.g., antibacterial agents), and combinations thereof.
1.8 Compositions 1.0-1.7 wherein the capsule encapsulates an oral active material, cosmetic agent, decorative agent, or combinations thereof.
1.9 Composition 1.8 wherein the oral active material is selected from an antibacterial agent, sensitivity agent, tooth-whitening or tooth-bleaching component, anti-calculus composition, anti-plaque agents, anti-gingivitis agents, anti-inflammatory agents, and combinations thereof.
1.10 Any of the preceding compositions further comprising a fluoride ion source.
1.11 Any of the preceding compositions further comprising fluoride source comprising a fluoride salt selected from stannous fluoride, sodium fluoride, potassium fluoride, sodium monofluorophosphate, sodium fluorosilicate, ammonium fluorosilicate, amine fluoride, ammonium fluoride, and combinations thereof.
1.12 Any of the preceding compositions comprising fluorophosphate.
1.13 Any of the preceding compositions comprising monofluorophosphate.
1.14 Any of the preceding compositions comprising a fluoride source in an amount of about 0.01 wt. % to about 2 wt. %, e.g., about 0.1 to about 0.2 wt. % of the total composition weight.
1.15 Any of the preceding compositions further comprising from about 500 to about 25,000 ppm, from about 1000 to about 4000, or about 1500, 2000, or 2500 ppm fluoride ion.
1.16 Any of the preceding compositions further comprising an abrasive.
1.17 Any of the preceding compositions comprising an abrasive is selected from a calcium phosphate (e.g., dicalcium phosphate dihydrate), calcium sulfate, precipitated calcium carbonate, silica (e.g. hydrated silica), and combinations thereof.

1.18 Any of the preceding compositions comprising calcium phosphate.

1.19 Any of the preceding compositions comprising hydrated silica.

1.20 Any of the preceding compositions comprising an abrasive in an amount of about 10 to about 90, or about 60 wt. % of the total composition weight.

1.21 Any of the preceding compositions comprising a small particle abrasive having a d50 of <5 micrometers.

1.22 Any of the preceding compositions comprising at least one surfactant.

1.23 Any of the preceding compositions comprising at least one surfactant selected from sodium lauryl sulfate, cocamidopropyl betaine, and combinations thereof.

1.2.4 Any of the preceding compositions comprising an anionic surfactant.

1.25 Any of the preceding compositions comprising sodium lauryl sulfate.

1.26 Any of the preceding compositions comprising at least one humectant.

1.27 Any of the preceding compositions comprising at least one humectant selected from glycerin, sorbitol and combinations thereof.

1.28 Any of the preceding compositions comprising at least one polymer.

1.29 Any of the preceding compositions comprising at least one polymer selected from polyethylene glycols, polyvinyl methyl ether maleic acid copolymers, polysaccharides (e.g. cellulose derivatives, for example carboxymethyl cellulose, or polysaccharide gums, for example xanthan gum or carrageenan gum), and combinations thereof.

1.30 Any of the preceding compositions comprising gum strips or fragments, or.

1.31 Any of the preceding compositions comprising flavoring, fragrance and/or coloring.

1.32 Any of the preceding compositions comprising water.

1.33 Any of the preceding compositions comprising an antibacterial agent.

1.34 Any of the preceding compositions comprising an antibacterial agent selected from triclosan, herbal extracts and essential oils (e.g. rosemary extract, thymol, menthol, eucalyptol, methyl salicylate), bisguanide antiseptics (e.g., chlorhexidine, alexidine car octenidine), quaternary ammonium compounds (e.g., cetylpyridinium chloride), phenolic antiseptics, hexetidine, povidone iodine, delmopinol, salifluor, metal ions zinc salts, for example, zinc citrate), sanguinarine, propolis and oxygenating agents (e.g., hydrogen peroxide, buffered sodium peroxyborate or peroxycarbonate).

1.35 Any of the preceding compositions comprising triclosan.

1.36 Any of the preceding compositions comprising an antibacterial agent in an amount of 0.01-5, 0.01-1.0, or about 0.3 wt. % of the total composition weight.

1.37 Any of the preceding compositions further comprising a physiologically acceptable potassium salt, e.g., potassium nitrate or potassium chloride, in an amount effective to reduce dentinal sensitivity.

1.38 Any of the preceding compositions comprising from about 0.1% to about 7.5% of a physiologically acceptable potassium salt, e.g., potassium nitrate and/or potassium chloride.

1.39 Any of the preceding compositions comprising water-hydratable film flakes of, e.g., a homogeneous mixture of a water-soluble hydroxyalkyl cellulose polymer and starch.

1.40 Any of the preceding compositions effective upon application to the oral cavity, e.g., with brushing, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) inhibit microbial biofilm formation in the oral cavity, (ix) reduce plaque accumulation, and/or (x) clean the teeth and oral cavity.

1.41 Any of the preceding compositions wherein the composition is toothpaste.

1.42 Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.43 Any of the preceding Compositions1.0-1.40 wherein the composition is a mouthwash.

In another embodiment, the invention encompasses a method to improve the oral health of a user comprising applying an effective amount of the dentifrice according to the invention to the oral cavity of a subject in need thereof, e.g., to i. reduce or inhibit formation of dental caries,
ii. reduce or inhibit demineralization and to promote remineralization of the teeth,
iii. reduce hypersensitivity of the teeth,
iv. reduce or inhibit gingivitis,
v. promote healing of sores or cuts in the mouth,
vi. reduce levels of bacteria in the mouth,
vii. raise and/or maintain pH at levels of at least pH 5.5,
viii. reduce plaque accumulation, and/or
ix. clean the teeth and oral cavity.

DETAILED DESCRIPTION OF THE INVENTION

The present invention is directed, in part, to capsules encapsulating any number of materials, distributed in an orally acceptable vehicle or carrier. The carrier can be a liquid, semi-solid, or solid phase, in the form of a mouth rinse, dentifrice (including toothpastes, toothpowders, and prophylaxis pastes), oral film, or any other form known to one of skill in the art. Conventional materials may be used to form the carriers listed above, and such materials are generally known to those of skill in the art. As recognized by one of skill in the art, the carriers and vehicles may including for example, surface active agents, such as surfactants, emulsifiers, and foam modulators, viscosity modifiers and thickeners, humectants, diluents, additional pH modifying agents, emollients, moisturizers, mouth feel agents, sweetening agents, flavor agents, colorants, preservatives, solvents, such as water, and combinations thereof. It is understood that while general attributes of each of the above categories of materials may differ, there may be some common attributes and any given material may serve multiple purposes within two or more of such categories of materials. The capsules of that are distributed in the dentifrices of the instant invention may be composed of conventional materials known to those of skill in the art, and are comprised of at least a matrix material, and a plasticizer.

Preferred matrix materials used in the capsules of present invention include polymers, e.g., polysaccharides, such as chitosan, algin, and agar. Preferably, the matrix materials are insoluble, or substantially insoluble in water. The amount of matrix material present will depend on the particular material selected, the vehicle or carrier selected, and may be easily determined by one of skill in the art.

Plasticizers are well known in the art, and include materials enable the capsules to deform, permanently or temporarily. Preferably, the plasticizers used in the present invention are generally recognized as safe, e.g., for use in the oral cavity. Such plasticizers include oil, such as mineral oil, naphthenic oil, and oils from plants, e.g., shea butter, macadamia ternifolia see oil, johoba (*Buxus chinensis*) oil, peanut oil, and combinations thereof. Other plasticizers useful include polymers, including polysaccharides, such as agar and algin, and other thickeners and binders which may also be present in the liquid phase of the mouthwash. Other plasticizers may include water, and humectants, such as glycerin, propylene glycol, and polyols, e.g., sorbitol, xylitol, and maltitol. Other plasticizers may include polyethers, such as polyethylene glycol and polysorbates.

The capsules may be comprised of other materials, such as vitamins (e.g., tocopherol), and excipients and inert ingredients, e.g., binders, fillers, anti-caking agents, disintegrants, colorants, flavorants, odorants, enzymes, coatings (e.g., enteric, acrylic, or carbohydrate or cellulosic coatings), chelants, preservatives (e.g., antibacterial agents), and the like. Preferred binders and fillers may include mica, titanium dioxide, and talc. Preservatives may include antimicrobial agents, such as phenoxyethanol, parabens methylparaben, ethylparaben, butylparaben, isobutylparaben, and propylparaben), and combinations thereof.

The amounts of the matrix, plasticizer, and optional other materials present in the capsule will depend on the particular materials selected. Preferably, the amount of matrix material, plasticizer, and other material present in the capsule is sufficient to maintain the shape of the capsule when the capsule is manufactured, filled, added to and mixed in the oral composition. Where the oral composition is a mouth wash, the capsules immediate rupture of the capsule when the mouthwash is used in the oral cavity, when the mouthwash is "swished" in the mouth. When the oral composition is a dentifrice or toothpaste, the capsules may rupture as a result of shear stress when the capsules are crushed between two hard surfaces, e.g., a surface of the oral cavity, or the bristles of toothbrush.

The capsules of the present invention may comprise from about 0.5% to about 25% matrix material, e.g., from about 0.5% to about 15%, or about 1%. 5%, or 10%. The capsules of the present invention may comprise from about 80% to about 99% of a plasticizer, including humectants, excipients, binders, fillers, and water. The capsules of the present invention may also comprise other materials, such as vitamins preservatives in an amount from about 0.5 to about 10%, e.g., about 1%, 2,%, 3%. 5% or about 7%.

The capsules are preferably evenly distributed within the oral compositions, and do not float to the top, or precipitate to the bottom of such compositions.

The oral care compositions according to the invention may include one or more fluoride ion sources, e.g., fluoride salts that may be soluble. A wide variety of fluoride ion-yielding materials can be employed as sources of soluble fluoride in the present compositions. Examples of suitable fluoride ion-yielding materials are found in U.S. Pat. No. 3,535,421 (Briner et al.); U.S. Pat. No. 4.885,155 (Parran, Jr. et al.), and U.S. Pat. No. 3,678,154 (Widder et al.), each incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate, as well as mixtures of two or more thereof.

In certain embodiments, the oral care composition of the invention may also contain a source of fluoride ions or fluorine-providing ingredient in amounts sufficient to supply from about 25 to about 25,000 ppm of fluoride ions, generally at least 500 ppm, e.g., 500-to-2000 ppm, e.g., 1000-1600 ppm., e.g., about 1450 ppm.

Fluoride ion sources may be added to the compositions of the invention at a level of about 0.01-to-about 10 wt. % in one embodiment, or about 0.03-to-about 5 wt. %, and in another embodiment, or about 0.1-to-about 1 wt. %, by weight of the composition, in still another embodiment. The weights of fluoride salts to provide the appropriate level of fluoride ion will obviously vary based on the weight of the counter ion in the salt.

The dentifrices of the invention may comprise a calcium phosphate abrasive, tricalcium phosphate phosphate ($Ca_3(PO_4)_2$), hydroxylapatite ($Ca_{10}(PO_4)_6(OH)_2$), or dicalcium phosphate dihydrate ($CaHPO_4 \cdot 2H_2O$).

The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and 30 microns, e.g., about between 5 and about 15 microns. The silica abrasives may be from precipitated silica or silica gels, such as the silica xerogels described in U.S. Pat. No. 3,538,230 (Pader et al.) and U.S. Pat. No. 3,862,307 (Digiulio), both incorporated herein by reference. Particular silica xerogels are marketed under the trade name Syloid® by W. R. Grace & Co., Davison Chemical Division. The precipitated silica materials include those marketed by the J. M. Huber Corp. under the trade name Zeodent®, including the silica carrying the designation Zeodent 115 and Zeodent 119. These silica abrasives are described in U.S. Pat. No. 4,340,583 (Wason), which is incorporated herein by reference.

In certain embodiments, abrasive materials useful in the practice of the oral care compositions in accordance with the invention include silica gels and precipitated amorphous silica having an oil absorption value of about less than 100 cc/100 g silica. e.g., in the range of about 45-to-about 70 cc/100 g silica, with oil absorption values being measured using the ASTA Rub-Out Method D281. In certain embodiments, the silicas are colloidal particles having an average particle size of about 3-to-about 12 microns, e.g., about 5-to-about 10 microns.

In particular embodiments, the abrasive materials comprise very small particles, e.g., having a d50<5 microns, for example, small particle silica (SPS) having a d50 of 3-4 microns, e.g., Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3-8% SPS- about 25-45% of a conventional abrasive.

Low oil-absorption silica abrasives particularly useful n the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29%, by weight, averaging about 7-to-about 10 microns in diameter, and an oil absorption of less than about 70 cc/100 g of silica, is an example of a low oil absorption silica abrasive useful in the practice of the present invention. The abrasive is present in the oral care composition of the present invention at a concentration of about 10-to-60%, by weight, e.g., in about 20-to-45%, by weight, e.g., in about 30-to-50%, by weight.

The oral care compositions of the invention also may include an agent to increase the amount of foam that is produced when the oral cavity is brushed. Illustrative examples of agents that increase the amount of foam include, but are not limited to, polyoxyethylene and certain polymers including, but not limited to, alginate polymers.

The polyoxyethylene (commonly known as polyethylene glycol ["PEG"] or polyethylene oxide) may increase the amount of foam and the thickness of the foam generated by the oral care carrier component of the present invention. The polyoxyethylenes suitable for this invention will have a molecular weight of about 200,000-to-about 7,000,000—in one embodiment, about 600,000-to-about 2,000.000, and in another embodiment about 800,000-to-about 1,000,000, with these high molecular weight polyoxyethylenes available under the trademark Polyox® from Union Carbide.

The polyoxyethylene may be present in an amount of about 1-to-about 90%, in one embodiment, about 5-to-about 50% and in another embodiment, and about 10-to-about 20%, by weight of the oral care carrier component of the oral care compositions of the present invention in still another embodiment. The amount of foaming agent in a single use of the dentifrice according to the invention is about 0.01-to-about 0.9%, by weight, in one embodiment, or about 0.05-to-about 0.5% by weight, in another embodiment, and in still another embodiment, about 0.1-to-about 0.2%, by weight.

Another agent optionally included in the oral care composition of the invention is a surfactant that is reasonably stable throughout a wide pH range, for example, an anionic, cationic, nonionic or zwitterionic surfactant, or a mixture of such compatible surfactants.

Suitable surfactants are described more fully, for example, in United States Patent (Gieske et al.) each of which is incorporated herein by reference.

In certain embodiments, the anionic surfactants useful herein include the water-soluble salts of alkyl sulfates having about 10-to-about 18 carbon atoms in the alkyl radical, and the water-soluble salts of sulfonated monoglycerides of fatty acids having about 10-to-about 18 carbon atoms. Sodium laurel sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8-to-about 18 carbon atoms, such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures of two or more thereof. Additional illustrative cationic surfactants include the quaternary ammonium fluorides described in U.S. Pat. No. 3,535.421 (Briner et al.), herein incorporated by reference. Certain cationic surfactants may also act as germicides in the compositions.

Illustrative nonionic surfactants that may be used in the compositions of the invention may be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the pluronics, polyethylene oxide condensates of alkyl phenols, products derived from the condensation of ethylene oxide with the reaction product of propylene oxide and ethylene diamine, ethylene oxide condensates of aliphatic alcohols, long-chain tertiary amine oxides, long-chain tertiary phosphine oxides, long-chain dialkyl sulfoxides and mixtures of such materials.

In certain embodiments, zwitterionic synthetic surfactants useful in the present invention may be broadly described as derivatives of aliphatic quaternary ammonium, phosphonium, and sulfonium compounds, in which the aliphatic radicals may be straight-chain or branched, wherein, when branched, one of the aliphatic substituents contains about 8-to-about 18 carbon atoms, and one contains an anionic water-solubilizing group, e.g., a carboxy, sulfonate, sulfate, phosphate or phosphonate group. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the dentifrice according to the invention comprises an anionic surfactant, e.g., sodium lauryl sulfate.

The surfactant or mixtures of compatible surfactants may be present in the compositions of the present invention in about 0.1-to-about 5.0%, in another embodiment, about 0.3-to-about 3.0% and in still another embodiment, about 0.5-to-about 2.0%, by weight of the total composition.

The oral care compositions of the invention may also include a flavoring agent. Flavoring agents that may be used in the practice of the present invention include, but are not limited to, essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1-to-about 5%, e.g., about 0.5-to-about 1.5%, by weight. The amount of flavoring agent in the individual oral care composition use is about 0.00 about 0.015%, by weight.

The oral care compositions of the invention also may optionally include one or more chelating agents able to complex calcium found in the cell walls of the bacteria in the mouth. Binding of this calcium weakens the bacterial cell wall and augments bacterial lysis.

A group of agents suitable for use as chelating agents in the present invention includes the soluble pyrophosphates, such as any of the alkali metal pyrophosphate salts. In certain embodiments, these salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0 wt. % pyrophosphate ions, e.g., about 1.5-to-about 6 wt. %. e.g., about 3.5-to-about 5 wt. % of such ions.

The oral care compositions of the invention also optionally include one or more polymers, such as polyethylene glycols, polyvinyl methyl ether maleic acid copolymers, polysaccharides (e.g., cellulose derivatives, for example, carboxymethyl cellulose, or polysaccharide gums, for example, xanthan gum or carrageenan gum). Acidic polymers, for example, polyacrylate gels, may be provided in the form of their free acids or partially- or fully-neutralized water-soluble alkali metal (e.g., potassium and sodium) or ammonium salts. Certain embodiments include 1:4-to-4:1 copolymers of maleic anhydride or acid with another polymerizable ethylenically-unsaturated monomer, for example, methyl vinyl ether (methoxyethylene), having a molecular weight (M.W.) of about 30,000-to-about 1,000,000. These copolymers are available, for example, as Gantrez AN 139 (M.W. 500;000), AN 119 (M.W. 250,000) and S-97 Pharmaceutical Grade (M.W. 70,000), from GAF Chemicals Corporation.

Other operative polymers for the instant dentifrices include the 1:1 copolymers of maleic anhydride with ethyl acrylate, hydroxyethyl methacrylate, N-vinyl-2-pyrollidone, or ethylene, the latter being available, for example, as Monsanto EMA No. 1103, M. W. 10,000 and EMA Grade 61, and 1:1. copolymers of acrylic acid with methyl or hydroxyethyl methacrylate, methyl or ethyl acrylate, isobutyl vinyl ether or N-vinyl-2-pyrrolidone.

Suitable generally, are polymerized olefinically- or ethylenically-unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group, or as part of a terminal methylene grouping. Illustrative of such acids are acrylic, methacrylic, ethacrylic, alpha-chloroacrylic, crotonic, beta-acryloxy propionic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. These copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylarnide 2 methylpropane sulfonic acid having a molecular weight of about 1,000-to-about 2.000,000, described in U.S. Pat. No. 4,842,847 (Zahid), which is incorporated herein by reference.

Another useful class of polymeric agents includes polyamino acids, particularly those containing proportions of anionic surface-active amino acids, such as aspartic acid, glutamic acid and phosphoserine, as disclosed in U.S. Pat. No. 4,866,161 (Sikes et al.), incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 (Dring et al.), U.S. Pat. Nos. 4.992,420; 4.355.022; 4,154,815; 4,058, 595; 3,991,177; and 3,696,191, all incorporated herein by reference. An enzyme of a mixture of several compatible enzymes in the current invention constitutes about 0.002-to-about 2.0% in one embodiment, or about 0.05-to-about 1.5% in another embodiment, or in yet another embodiment, about 0.1-to-about 0.5%.

Water may also be present in the oral compositions of the invention. Water, employed in the preparation of commercial oral compositions should be deionized and free of organic impurities. Water commonly makes up the balance of the compositions according to the invention, e.g., and includes about 4-to-about 90%, e.g., about 20-to-about 60%, or, e.g., about 10% to about 30%, by weight of the oral compositions, but, in no case, enough to dissolve the capsules or, if present, the rapidly-hydratable film flakes, in the dentifrices. This amount of water includes the free water which is added plus that amount which is introduced with other materials, such as with sorbitol, or with any other components of the invention.

Within certain embodiments of the oral compositions, it is also desirable to incorporate a humectant to prevent the composition from hardening upon exposure to air. Certain humectants may also impart desirable sweetness or flavor to dentifrice compositions. The humectant, on a pure humectant basis, generally includes about 15-to-about 70% in one embodiment, or about 30-to-about 65% in another embodiment, by weight of the dentifrice composition.

Suitable humectants include consumable polyhydric alcohols, such as glycerine, sorbitol, xylitol, propylene glycol, as well as other polyols and mixtures of these humectants. Mixtures of glycerine and sorbitol may be used in certain embodiments as the humectant component of the toothpaste compositions herein.

In addition to the above-described components, the embodiments of this invention can contain a variety of optional dentifrice ingredients, some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597 (Majeti);

U.S. Pat. No. 3,959,458 (Agricola et al.) and U.S. Pat. No. 3,937,807 (Haefel), all being incorporated herein by reference.

Antibacterial agents may be used in the compositions of the present in invention, and may be present in amounts of about 0.001-to-about 3.0%, by weight of the compositions. A non-limiting of useful additional oral care compounds includes non-ionic antibacterial agents, including phenolic and bisphenolic compounds, such as halogenated diphenyl ethers, including triclosan (2,4,4'-trichloro-2'-hydroxy-diphenylether), triclocarban (3,4,4-trichlorocarbanilide), as well as 2-phenoxyethanol, benzoate esters, carbanilides, one or more basic amino acids, e.g., arginine, in free base or salt form, and combinations of two or more thereof. Such agents may be added in effective amounts, e.g., from about 1-to-about 20%, by weight based on the total weight of the composition, depending on the agent chosen. A halogenated diphenyl ether, such as triclosan, may be present in an amount of about 0.3%, by weight of the oral composition, for example.

The compositions of the present invention may incorporate one or more antisensitivity agents, e.g., potassium salts, such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from about 1-to-about 20%, by weight based on the total weight of the composition, depending on the agent chosen. The compositions of the present invention may also be used to treat hypersensitivity by blocking dentin tubules when applied to a tooth.

The compositions of the present invention may also include a tooth-whitening or tooth-bleaching component, which are known in the art. Suitable whitening and bleaching components include peroxides (such as hydroperoxides, hydrogen peroxide, peroxides of alkali and alkaline earth metals [such as lithium peroxide, potassium peroxide, sodium peroxide, magnesium peroxide, calcium peroxide, barium peroxide, and mixtures of two or more thereof], organic peroxy compounds, peroxy acids, and mixtures of two or more thereof), metal chlorites (such as calcium chlorite, barium chlorite, magnesium chlorite, lithium chlorite, sodium chlorite, and potassium chlorite), persulfates, perborate, urea peroxide, and mixtures of two or more thereof. Such agents may be added in effective amounts, e.g., from about 1-to-about 20%, by weight based on the total weight of the composition, depending on the agent chosen.

The oral composition optionally comprises an anti-calculus composition, such as, for example, one or more of the anti-calculus compositions discussed in U.S. Pat. No. 5,292,526 (Gaffar et al.). In various embodiments, the anti-calculus composition includes one or more polyphosphates. The anti-calculus composition may include at least one wholly- or partially-neutralized alkali metal or ammonium tripolyphosphate or hexametaphosphate salt present in the oral composition in an effective anti-calculus amount. The anti-calculus active may also include at least one water-soluble, linear molecularly-dehydrated polyphosphate salt effective in an anti-calculus amount. The anti-calculus active may also include a mixture of potassium and sodium salts, at least one of which is present in an effective, anti-calculus amount as a polyphosphate anti-calculus agent. The ratio of potassium-to-sodium in the composition may be up to less than 3:1. The polyphosphate may be present in the oral composition in various amounts, such as an. amount wherein the weight ratio of polyphosphate ion to anti-bacterial agent ranges from in excess of 0.72:1 to less than 4:1, or wherein the weight ratio of the anti-bacterial-enhancing agent-to-the polyphosphate ion ranges from about 1:6 to about 2.7:1. Other useful anticalculus agents include polycarboxylate polymers and polyvinyl methyl ether/maleic anhydride (PVM/MA) copolymers, such as those marketed under the trademark GANTREZ® (by whom?).

The film flakes that may, optionally, be present in dentifrices of the instant invention may be formed from a matrix comprised of hydroxyalkyl methylcellulose starch and starch film forming agents in which is entrained a colorant, such a dye or pigment, a flavorant, sweetener and/or a therapeutic agent, such as an antibacterial agent or breath-freshening agent, and may further comprise water, additional film-forming agents, plasticizing agents, surfactants and/or emulsifying agents. In preparing the film matrix according to the present invention the hydroxyalkylmethyl cellulose, a starch ingredient, a colorant, flavor, sweetener and/or therapeutic agents, and, optionally, other film forming ingredients, are dissolved in a compatible solvent to form a film-forming composition, which is cast on a releasable carrier and dried to form a sheet of film matrix material. The carrier material must have a surface tension that allows the film solution to spread evenly across the intended carrier width without soaking to form a destructive bond between the film carrier substrates. Examples of suitable carrier materials include glass, stainless steel, Teflon® and polyethylene-impregnated paper. Drying of the film may be carried out at high temperature using a drying oven, drying terminal, vacuum drier, or any other suitable drying equipment that does not adversely effect the ingredients of which the film is composed. The film thickness ranges in size from 0.5-to-10, preferably 2-to-3 microns. The dried film of the present invention is then cut or punched into shaped flakes having a particle size of 0.01-to-0.50, preferably 0.08-to-0.25 inches. Additional stability may be provided to the shapes formed from the dried film by applying to the film, before shaping into flakes, a protective barrier overcoat, such as a food-grade shellac or ethyl cellulose. When the film is to be used for decorative effect, the film once formed is punched into various attractive shaped flakes, such as hearts, stars, diamonds and circles. The film flakes are incorporated in the base compositions of the present invention at a concentration of about 0.05-to-1.0%, preferably 0.1-to-about 0.5%, by weight. The major film-forming agent used to prepare the film matrix of the present invention is an hydroxyalkyl cellulose, such as hydroxypropyl methyl cellulose, hydroxyethylpropyl cellulose, hydroxybutyl methyl cellulose, hydroxy propyl methyl cellulose or carboxymethyl cellulose. Preferably the cellulose polymer is a low viscosity hydropropylmethyl cellulose polymer (HPMC, available commercially from the Dow Chemical Company under the trade designation Methocel E5 LV, a USP grade, low viscosity HPMC having 29.1% methoxyl groups and 9% hydroxyproxyl group substitution, as a white or off-white free-flowing dry powder, with a viscosity [as measured with a Ubbelohde tube viscometer] of 5.1 mPa·s at 20° C. as a 2 wt. % solution in water). When HPMC is used as the film-forming agent it is preferred that the HPMC have a viscosity in the range of about 1 to about 40 millipascal seconds (mPa·s) as determined as a 2% by weight aqueous solution of the HPMC at 20° C. using a Ubbelohde tube viscometer. Preferably the HPMC has a viscosity of about 3 to about 20 mPa·s at 20° C. The hydroxyalkyl methyl cellulose is incorporated in the film matrix in amounts ranging from about 10-to-about 60, preferably about 15-to-about 40%, by weight.

Cold water-swellable, physically-modified and pregelatinized starches (available under the trade designation Cerestar Polar Tex-Instant 12640 from the Cerestar Company as a pregelatinized, stabilized and crosslinked waxy maize starch, with excellent cold storage and freeze-thaw stability, a rapid hydration rate, an ability to reach extremely high viscosity without cooking, is readily dispersible and swellable in cold water, has a smooth and creamy texture similar to cook-up starches, particularly useful as texture modifier to increase the stiffness of the hydroxyalkyl methyl cellulose film matrix of these flakes, excellent paste clarity and a bland flavor, and in its dry form, is a white free-flowing powder with an average flake size no greater than 180 micrometers, with 85% of the flakes being smaller than 75 micrometers, and a bulk density of 44 lbs/ft$^3$).

In the preparation of such starch products, the granular starch is cooked in the presence of water, and possibly an organic solvent, at a temperature not higher than 10° C. higher than the gelatinization temperature. The obtained starch is then dried.

The pregelatinized starch is present in the film matrix of the present invention in an amount ranging from about 5-to-about 50, preferably about 10-to-about 35%, by weight. The hydroxyalkyl cellulose-to-starch ratio (by weight) may vary from about 1:3-to-about 4:1, preferably about 1:1.5-to-about 2.5:1.

The film flakes may also be prepared with colorants, and the colorants are pharmacologically- and physiologically-non-toxic when used in the suggested amounts. The colorants include both pigments (including non-toxic, water-insoluble inorganic pigments, such as titanium dioxide, titanium dioxide coated mica (Timiron), chromium oxide greens, ultramarine blues and pinks and ferric oxides, as well as water-insoluble dye lakes prepared by extending calcium or aluminum salts of FD&C dyes on alumina, such as FD&C Green #1 lake, FD&C Blue 190 2 lake. FD&C R&D #30 lake and FD&C # Yellow 15 lake- each having a flake size in the range of 5 to 1000 microns, preferably 250 to 500 microns) and dyes. Pigments are incorporated in the decorative film matrix of the flakes in an amount ranging from about 1-to-about 10, preferably about 2-to-about 5%, by weight.

The compositions of the present invention may be made using methods which are common in the oral care product area.

The method aspect of the present invention involves applying to the oral cavity, according to known methods, a safe and effective amount of a composition described herein.

The compositions and methods according to the invention are useful in a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit precarious lesions of the enamel. Finally, by increasing the pH in the mouth and discouraging pathogenic bacteria, the dentifrices according to the instant invention are useful to promote healing of sores or cuts in the mouth.

The compositions and methods according to the invention may be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention, as many variations are possible without departing from the spirit and scope thereof. Various modifications of the invention in addition to those shown and described herein should be apparent to those skilled in the art and are intended to fall within the appended claims.

EXAMPLE 1

Dentifrice compositions according to the present invention are prepared with the following materials as indicated on a percent weight basis:

| | |
|---|---|
| Sodium CMC | 0.7% |
| Polyethylene glycol 600 | 3% |
| Sorbitol, non crystallizing | 56% |
| Sodium saccharin | 0.3% |
| Fluoride ion source | 0.2% |
| Sodium pyrophosphate | 0.5% |
| Abrasive | 24% |
| Cocamidopropyl betaine | 1.3% |
| SLS | 5% |
| Color | .01% |
| Other flavor | 1.3% |
| Capsules | 2% |
| Water | Q.S. 100% |

We claim:

1. An oral care composition comprising capsules encapsulating one or more flavors, said capsules distributed in an orally acceptable vehicle or carrier,
   wherein said capsules are containers made of material that is substantially non-porous to said encapsulated flavors, said container material comprising:
   from about 80% to 99% by weight of a plasticizer selected from the group consisting of mineral oil, naphthenic oil, shea butter, macadamia temifolia seed oil, jojoba oil, peanut oil, glycerin, propylene glycol, sorbitol, xylitol, maltitol, polyethers and combinations thereof, and
   a matrix material which is a combination of chitosan, algin and agar wherein the matrix material comprises 0.5% to 25% by weight of the capsules,
   wherein the capsules are deformable.

2. The composition of claim 1, wherein the capsules further comprise a vitamin.

3. The composition of claim 1, wherein the capsules further comprise excipients and inert materials selected from the group consisting of binders, fillers, anti-caking agents, disintegrants, colorants, flavorants, odorants, enzymes, coatings, chelants, preservatives, and combinations thereof.

4. The composition of claim 1, wherein the capsules further comprise an oral active material selected from the group consisting of antibacterial agent, sensitivity agent, tooth-whitening or tooth-bleaching component, anti-calculus composition, anti-plaque agents, anti-gingivitis agents, anti-inflammatory agents, and combinations thereof.

5. The composition of claim 1, further comprising a fluoride ion source.

6. The composition of claim 5, wherein the fluoride ion source is present in an amount of about 0.01% to about 2% by weight.

7. The composition of claim 5, comprising from about 500 to about 25,000 ppm of fluoride ion.

8. The composition of claim 4, further comprising an abrasive.

9. The composition of claim 8, further comprising a surfactant.

10. The composition of claim 9, wherein the surfactant is selected from the group consisting of sodium lauryl sulfate, cocamidopropyl betaine, and a combination thereof.

11. The composition of claim 9, wherein the orally acceptable vehicle or carrier comprises a humectant.

12. The composition of claim 11, wherein the humectant is selected from the group consisting of glycerin, sorbitol and a combination thereof.

13. The composition of claim 12, wherein the orally acceptable vehicle or carrier comprises a polymer selected from the group consisting of a polyethylene glycol, a polyvinyl methyl ether maleic acid copolymer, a polysaccharide, and a combination thereof.

14. The composition of claim 13, comprising an antibacterial agent selected from the group consisting of triclosan, a herbal extract or essential oil, a bisguanide antiseptic, a quaternary ammonium compound, a phenolic antiseptic, hexetidine, povidone iodine, delmopinol, salifluor, a metal ion, sanguinarine, propolis and an oxygenating agent.

15. The composition of claim 14, wherein the antibacterial agent is present in an amount of 0.01% to 5% by weight of the total composition weight.

16. The composition of claim 1, further comprising one or more water-hydratable film flakes.

17. The composition of claim 1, which is a toothpaste.

18. The composition of claim 1, which is a mouthwash.

19. The composition of claim 13, wherein the polysaccharide is selected from the group consisting of carboxymethyl cellulose, xanthan gum, carrageenan, and a combination thereof.

20. The composition of claim 14, wherein the herbal extract or essential oil is selected from the group consisting of rosemary extract, thymol, menthol, eucalyptol, methyl salicylate, and a combination or two or more thereof.

21. The composition of claim 1, wherein the composition further comprises 10% to 60% by weight of at least one abrasive,
   wherein the capsules comprise 0.5% to 25% by weight of matrix material which is a combination of chitosan, algin and agar; and
   about 80% to 99% by weight of a plasticizer selected from the group consisting of mineral oil, naphthenic oil, shea butter, macadamia ternifolia seed oil, jojoba oil, peanut oil, glycerin, propylene glycol, sorbitol, xylitol, maltitol, polyethers and combinations thereof,
   wherein the abrasive materials comprise a small particle abrasive and a second larger particle abrasive selected from the group consisting of a calcium phosphate, calcium sulfate, precipitated calcium carbonate, silica, and combinations thereof, and said small particles abrasive has a d50 <5 microns.

* * * * *